United States Patent [19]

MacGregor et al.

[11] Patent Number: 5,416,245

[45] Date of Patent: May 16, 1995

[54] SYNERGISTIC PROCESS FOR THE PRODUCTION OF METHANOL

[75] Inventors: Norman J. MacGregor, Kincardine; Gerry Shessel, North York, both of Canada

[73] Assignee: Integrated Energy Development Corp., Kincarding, Canada

[21] Appl. No.: 152,319

[22] Filed: Nov. 12, 1993

[51] Int. Cl.⁶ .................. C07C 27/14; C07C 43/04
[52] U.S. Cl. .................... 568/697; 58/703; 58/704
[58] Field of Search ............... 518/703, 704; 568/697

[56] References Cited

U.S. PATENT DOCUMENTS

| | | |
|---|---|---|
| 2,482,284 | 9/1949 | Michael et al. |
| 3,095,699 | 7/1963 | Bauer. |
| 4,115,467 | 9/1978 | Fowler .............. 518/703 |
| 4,476,249 | 10/1984 | Avery .............. 518/703 |
| 4,528,811 | 7/1985 | Stahl. |
| 4,534,772 | 8/1985 | Reichl. |
| 4,592,762 | 6/1986 | Babu et al. |
| 4,699,632 | 10/1987 | Babu et al. |
| 4,773,981 | 9/1988 | Bidwell. |
| 4,810,417 | 3/1989 | Diemer et al. |
| 4,833,170 | 5/1989 | Agee. |
| 4,899,544 | 2/1990 | Boyd. |
| 4,942,734 | 7/1990 | Markbreiter et al. |
| 5,023,276 | 6/1991 | Yarrington et al. |
| 5,025,631 | 6/1991 | Garbo. |
| 5,026,529 | 6/1991 | Harandi et al. |
| 5,070,016 | 12/1991 | Hallberg. |
| 5,132,007 | 2/1992 | Meyer et al. |

Primary Examiner—Johann Richter
Assistant Examiner—Michael B. Hydorn
Attorney, Agent, or Firm—Philip Mendes da Costa

[57] ABSTRACT

A synergistic process for the production of methanol comprises electrolysing water to produce hydrogen and oxygen; providing a feed stream of an organic combustible fuel; feeding at least a portion of the oxygen together with a stoichiometric amount of the organic combustible fuel to a partial oxidation reactor to produce off gases including carbon monoxide and hydrogen; feeding a stoichiometric amount of carbon monoxide and hydrogen to a methanol synthesizer to produce methanol. Further, the process utilizes the methanol and off gases and supplies of hydrocarbons and ethanol to produce MTBE and/or ETBE.

34 Claims, 11 Drawing Sheets

5,416,245

SYNERGISTIC PROCESS FOR THE PRODUCTION OF METHANOL

FIELD OF THE INVENTION

This invention relates to an integrated, synergistic method of producing methanol wherein the release of green house gases is substantially reduced and, preferably, are negligible. The invention also relates to a method of producing lower alkyl tertiary butyl ethers via a partial oxidation process of heavy hydrocarbon fractions wherein the release of green house gases is substantially reduced or, preferably, is negligible.

BACKGROUND OF THE INVENTION

Lower alkyl tertiary butyl ethers, such as methyl tertiary butyl ether (MTBE) and/or ethyl tertiary butyl ether (ETBE) may be added to gasoline as an oxygenate. Such ethers are relatively low volatility components which may be used to improve the octane rating of gasoline.

These ethers may be produced from methanol. A common process for the production of methanol is steam reformation. According to this process, methane is reacted with steam at high temperatures and pressures. Traditionally, natural gas is used as a source of methane. Pursuant to this process, less than 85% of the natural gas is converted to methanol. The remainder of the natural gas is used as fuel for the process. One disadvantage of the steam reformation process is that it utilizes a valuable commercial product, namely natural gas, to produce methanol. A further disadvantage of steam reformation is that it results in the release of substantial quantities of green house gases.

An alternate route for the production of methanol is the Texaco gasification process. According to this process, a hydrocarbon feedstock, such as natural gas, is subjected to partial oxidation with pure oxygen to produce carbon monoxide and hydrogen. The oxygen is obtained from a cryogenic plant. Subsequently, carbon monoxide and oxygen are fed in stoichiometric proportions to a methanol synthesizer.

As a further alternative, a heavy oil distillate, of low value, can be used as a feedstock to the partial oxidation process to put the oil to higher value uses. The molar ratio of carbon monoxide and hydrogen in the resulting feedstock to the methanol synthesizer is approximately one to two. The required molar ratio is one to four to affect methanol synthesis. Accordingly, the mixture of carbon monoxide and hydrogen is subjected to a water shift process which converts approximately half of the carbon monoxide, that is the carbon derived from the feedstock oil and the oxygen derived from the cryogenic separation to carbon dioxide. Subsequently, the carbon dioxide must be separated from the feed stream requiring extensive and costly capital equipment and ongoing operating expense. Subsequently, carbon monoxide and hydrogen in the appropriate stoichiometric proportions are fed to a reactor to produce methanol. One disadvantage with this process is that a cryogenic plant is required to produce oxygen for the partial oxidation reaction. A further disadvantage of this process is that the water shift reaction is required to obtain stoichiometric amounts of carbon monoxide and hydrogen for the methanol synthesizer. Further, in this process, substantially half of the carbon monoxide i.e. carbon and oxygen are converted to carbon dioxide which is of no further contribution to this process. The high level of carbon dioxide, a greenhouse gas, produced effectively negates the environmentally beneficial aspect of utilizing methanol fuels and is a very considerable waste of usable energy. Accordingly, the use of low value heavy oil, which is abundant, is not cost competitive with higher value natural gas consumption.

SUMMARY OF THE INVENTION

Pursuant to this invention there is provided a synergistic process for the production of methanol comprising the steps of:

(a) electrolysing water to produce hydrogen and oxygen;

(b) providing a feed stream of an organic combustible fuel;

(c) feeding at least a portion of the oxygen produced in step (a) together with a stoichiometric amount of said organic combustible fuel to a partial oxidation reactor to produce off gases including carbon monoxide and hydrogen;

(d) feeding at least a portion of said carbon monoxide and hydrogen to a methanol synthesizer to produce methanol; and, (e) adding additional hydrogen to said methanol synthesizer to provide a stoichiometric feed of hydrogen and carbon monoxide to said methanol synthesizer.

Pursuant to a further embodiment of this invention, the process comprises the steps of:

(a) electrolysing water to produce hydrogen and oxygen;

(b) providing a feed stream of an organic combustible fuel;

(c) feeding at least a portion of the oxygen produced in step (a) together with a stoichiometric amount of said organic combustible fuel to a partial oxidation reactor to produce off gases including carbon monoxide and hydrogen;

(d) providing a feed stream of carbon dioxide to cool said partial oxidation reactor so as to elevate the temperature of said carbon dioxide to a temperature above the dissociation temperature of said carbon dioxide;

(e) feeding said heated carbon dioxide to said partial oxidation reactor;

(f) feeding at least a portion of said carbon monoxide and hydrogen to a methanol synthesizer to produce methanol; and, (g) adding additional hydrogen to said methanol synthesizer to provide a stoichiometric feed of hydrogen and carbon monoxide to said methanol synthesizer.

In a further alternative embodiment, the methanol may be combined with isobutylene to produce methyl tertiary butyl ether. In a further optional embodiment, the process may also include an isobutylene synthesizer wherein butane and steam are combined to produce isobutylene and hydrogen.

One advantage of the instant invention is the use of electrolysis to produce pure oxygen and pure hydrogen. An electrolysis unit may be operated using surplus energy available from power utility companies. Traditionally, power utility companies have reduced demand for electricity at evenings and on weekends. However, for reasons of efficiency, it is preferred to maintain the generating plants operating on a continual basis. Accordingly, there are substantial quantities of surplus power available at very low cost. The surplus power may be utilized to produce very high purity hydrogen and oxygen. The hydrogen and oxygen may be stored for use as may be required in the production of carbon monoxide.

A further advantage of the instant process is that the use of electrolysis results in the production simultaneously of oxygen for the partial oxidation reactor and hydrogen which may be used to obtain a stoichiometric balance of carbon monoxide to hydrogen which is fed to the methanol synthesizer.

The hydrogen for the methanol synthesizer may be supplied from the partial oxidation reaction as well as a by-product of the production of isobutylene. In such an embodiment, the hydrogen from the electrolysis unit, which is essentially pure, may be collected and sold as a commercial product.

The process is particularly well adapted to utilize a heavy hydrocarbon fraction, such as a gas oil or a residual oil from the cracking of crude petroleum. The process has numerous sources for hydrogen, such as from the production of isobutylene or from the partial oxidation reactor which may be utilized to obtain a stoichiometric amount of hydrogen for addition to the methanol synthesizer without utilizing the high quality hydrogen produced by the electrolysis plant or without carrying out a water shift reaction.

An ethanol fermenter may also be included in the process. An alcohol precursor and steam may be supplied to an ethanol fermenter to produce ethanol. The ethanol may be reformed, using the isobutylene, to produce ETBE and additional quantities of hydrogen to be used to increase methanol production.

In a further alternate embodiment, a producer gas reactor may be optionally added. The producer gas reactor heats carbon dioxide, such as carbon dioxide from an ethanol fermenter, to produce carbon monoxide. The carbon monoxide is utilized as additional feedstock for the methanol synthesizer. The increase in the amount of carbon monoxide fed to the methanol synthesizer requires a requisite increase in the amount of hydrogen fed to the methanol synthesizer. The increased requirement for hydrogen for the methanol synthesizer may be obtained as a by-product from the isobutylene synthesizer. If required, additional hydrogen may be obtained from the electrolysis.

According to a further alternate embodiment, a cogeneration plant may be included in the process. In the cogeneration plant, a portion of the hydrocarbon feedstock may be combusted to produce steam, electricity and flue gases. The electricity could be used to power the electrolysis unit. The steam could be used in various places throughout the process such as compressing gases, pumping fluids, heating steps in the process such as fermentation, distillation, and others. The flue gases may also be used to provide a source of carbon dioxide for a producer gas reactor. Accordingly, the addition of a cogeneration unit could also be utilized to produce an efficient, integrated process for the production of MTBE and ETBE while substantially reducing or eliminating the release of green house gases.

In a further alternate embodiment of the instant process, carbon dioxide from vented gas or the atmosphere may be passed through a heat exchanger which is attached to the partial oxidation reactor. The carbon dioxide would be heated by the reaction products of the partial oxidation reactor to or above the dissociation temperature of carbon dioxide. Once heated to that temperature, the carbon dioxide would dissociate to form carbon monoxide which may be subsequently be fed to the methanol synthysizer and oxygen which may be fed to the partial oxidation reactor.

BRIEF DESCRIPTION OF THE DRAWINGS

These and other advantages of the instant invention may be more completely and fully understood by means of the following description of the accompanying drawings of the preferred embodiment of the process which is the subject of this invention and in which.

DESCRIPTION OF THE PREFERRED EMBODIMENT

Figure 1:
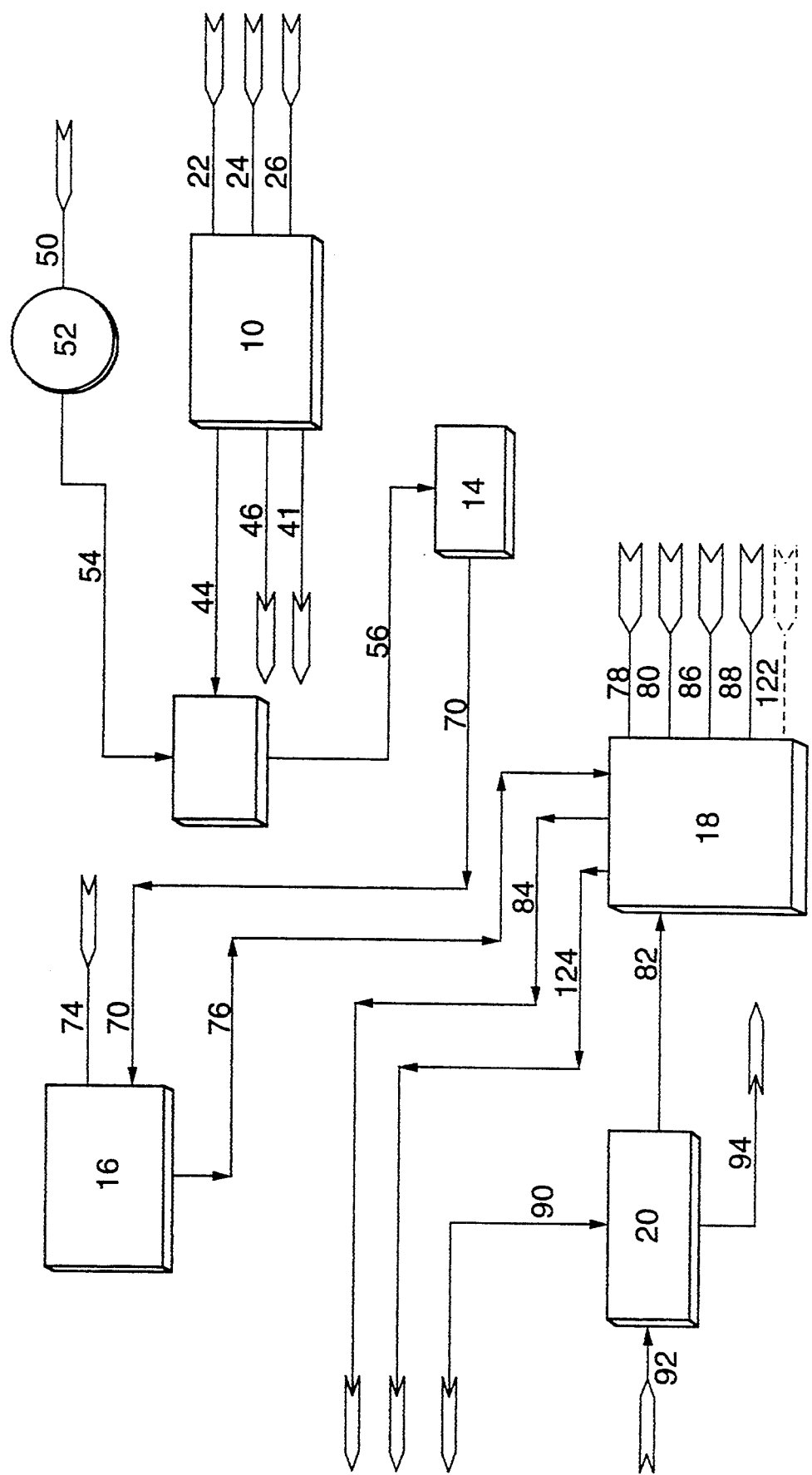
FIG. 1 is a schematic of a process flow sheet of one embodiment of this invention.

As shown in FIG. 1, according to the preferred embodiment, the process comprises electrolysis unit 10, a partial oxidation reactor 12, gas cleaning unit 14 and a methanol synthesizer 16. The process may also include an ether synthesizer 18 for the production of lower alkyl tertiary butyl ethers as well as isobutylene synthesizer 20.

Figure 6:
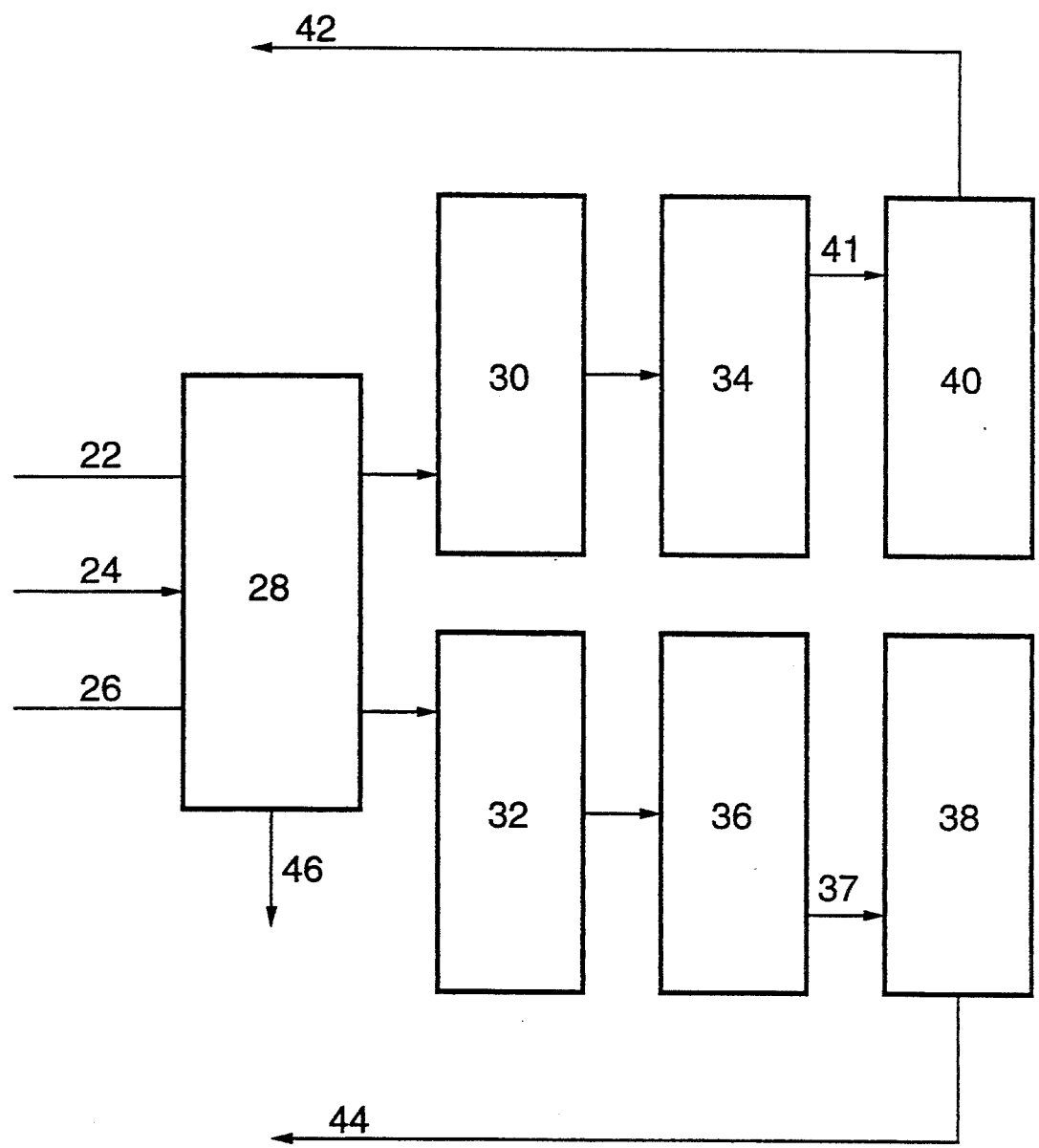
FIG. 6 is a schematic of a process flow sheet for the electrolysis plant shown in FIGS. 1, 2, 3 and 4.

Electrolysis plant 10 utilizes electricity to produce hydrogen, oxygen and, optionally, heavy water ($D_2O$). Electricity is fed via conduit 22 to the electrolysis plant. Electrolysis cells which electrolyse water typically run on direct current. Accordingly, electricity fed to electrolysis plant 10 is fed to a direct current rectifier (not shown) to produce direct electrical current which is then used by the electrolysis cells in electrolysis plant 10. Water, such as in the form of a condensate of boiler feedwater, and an electrolyte such as sodium hydroxide, are supplied via process streams 24 and 26 respectively to the electrolysis unit 10. As shown in FIG. 6, electrolysis unit 10 may comprise a plurality of electrolysis cells 28 which are utilized to electrolyse water into hydrogen and oxygen. The hydrogen and oxygen are separated by conventional means and may be transferred to vessels 30 and 32 respectively. The hydrogen and oxygen may then be compressed by compressors 34 and 36 respectively. The compressed oxygen may then be stored in storage vessel 38. Similarly, the compressed hydrogen may be stored in hydrogen storage vessel 40. Storage vessels 38 and 40 provide pools of oxygen and hydrogen which may be used as required in the process. Hydrogen is provided to storage vessel 40 via feed stream 41 and oxygen is provided to storage vessel 38 via feed stream 37. If heavy water is produced via electrolysis cells 28, then heavy water is supplied to a suitable storage vessel (not shown) by process stream 46.

Electrolysis is a very energy intensive process. According to the instant process, the electricity which is used in electrolysis unit 10 is surplus electricity which may available on off-peak hours at very low cost from power utility corporations. Alternately, as discussed below, a cogeneration reactor may also form part of the process. The cogeneration reactor may be operated on a continual basis to produce process steam for use in an industry. However, the demand for electricity may drop off at night or on weekends. In these off-peak hours, the electricity may not be required and may then be used to run electrolysis cells 28. Similarly, power utilities typically run several generating stations during the day to supply businesses and industry with electricity. On evenings and on weekends, industries slow down or shut down and accordingly require less electricity. However, the generating facilities may be kept operative during these periods and excess power is then available at greatly reduced rates for utilization in the process of the instant invention. Accordingly, by the instant process, the electrolysis plant may be used for converting surplus electrical energy into stored chemical energy (namely in the form of oxygen and hydrogen). The stored chemical energy is then available for use at a convenient time at a facility which operates the process of the instant invention.

Partial oxidation reactor 12 comprises a partial oxidation reactor for converting a hydrocarbon source substantially to carbon monoxide and hydrogen. The other partial oxidation gases may include small amounts of steam, carbon dioxide and hydrogen sulfide. The specific gases which are produced by the partial oxidation reactor depend, in part, on the make up of the hydrocarbon feedstock. Preferably, the hydrocarbon feedstock which is used in the instant process is a relatively low value product and preferably comprises a heavy oil such as gas oil (which has a boiling point above about 650° F.) or a residual oil (which has a boiling point above about 1000° F.) from petroleum refining. Typically, these petroleum products have a ratio hydrogen to carbon of about 2:1.

As shown in FIG. 1, oil may be shipped via a pipe 50 to storage vessel 52. Oil is transported from storage vessel 52 via process stream 54 to partial oxidation reactor 12. Oxygen is fed via process stream 44 from electrolysis unit 10 to partial oxidation reactor 12. Preferably, partial oxidation reactor 12 utilizes a non-catalytic, partial oxidation process in which the hydrocarbon feedstock is reacted at a high temperature and usually a high pressure with oxygen, oxygen-enriched air or air. Preferably, as shown in FIG. 1, oxygen from the electrolysis unit 10 is utilized in partial oxidation reactor 12. The process produces principally carbon monoxide and hydrogen with some carbon dioxide, steam and, if the feed contains sulfur, hydrogen sulphide. The process effectively consumes the feedstock without producing heavy hydrocarbons, tar or other potentially troublesome by-products such as oxides of sulphur or nitrogen.

Typically, the partial oxidation reactor is operated at a temperature between about 1200° C. and about 1500° C. The operating pressure is preferably from about 15 to about 85 bars. At these process conditions, substantially all of the hydrocarbon feedstock is converted to off gases. The gas exiting the partial oxidation reactor may be cooled by direct contact with water in a quench chamber or may be used to power a waste heat boiler by an indirect heat exchanger (not shown). Alternately, as discussed below, the gas may be cooled by an incoming stream of carbon dioxide.

An advantage of the partial oxidation reactor is that a portion of the hydrocarbon fuel is not utilized to produce heat for the process. This compares to steam methane reformation wherein about 15%, or more, of the natural gas feedstock is consumed to power the process. A further advantage of the instant invention is that, due to the highly reducing atmosphere of the reactor, no nitrous oxides, sulfur oxides or carbon dioxide emissions are created. Partial oxidation reactor 12 operates on a zero emission basis, i.e. the emission of harmful green house gases is substantially negligible.

The off gases from the partial oxidation reactor are transported via process stream 56 to gas cleaning unit 14. Gas cleaning unit 14 treats the off gases to remove undesirable compounds from the carbon monoxide and hydrogen. For example, during the partial oxidation reaction, hydrogen sulphide may be produced. Hydrogen sulphide poisons the catalyst used in methanol synthesizer 16. Accordingly, harmful amounts of hydrogen sulphide must be removed. The hydrogen sulphide may be removed by use of an amine-based process such as one which utilizes MDEA. Other by-products, such as steam, or the oxides of trace metalic elements may be removed.

Gas cleaning unit 14 produces a substantially pure stream of carbon monoxide and hydrogen 70. If a heavy oil is used as the feedstock, then the ratio of carbon monoxide to hydrogen in the off gases is approximately 1:1 (i.e. 2 hydrogen atoms for each carbon atom). Methanol contains 4 hydrogen atoms for each carbon atom. Accordingly, additional make up hydrogen must be supplied so that stoichoimetric amounts of carbon monoxide and hydrogen may be supplied to methanol synthesizer 16.

Methanol synthesizer 16 converts carbon monoxide and hydrogen to methanol. Carbon monoxide and hydrogen are fed to the methanol synthysizer via process stream 70 and additional hydrogen may be fed to the methanol synthysizer by process stream 74. Additional hydrogen stream 74 is utilized to ensure that a substantially stoichiometric amount of hydrogen and carbon monoxide are fed to methanol synthesizer 16. As discussed above, depending upon the feedstock which is utilized, additional hydrogen may be required to provide at least an approximate stoichiometric amount of carbon monoxide and hydrogen. The methanol may be stored in a storage vessel (not shown) or sold as a commodity into the market place. Alternately, some or all of the methanol may be sent via process stream 76 to ether synthesizer 18. The flow of carbon monoxide and hydrogen to methanol synthesizer 16 is preferably in stoichiometric proportion. Accordingly, the molar ratio of carbon monoxide to hydrogen gas is preferably about 1:2 (i.e. four hydrogen atoms for each carbon atom).

The hydrogen for methanol synthesizer 16 may be obtained from a hydrogen storage vessel. The vessel may contain hydrogen obtained from electrolysis unit 10 and/or isobutylene synthesizer 20 and/or any available source. As will be appreciated, if a heavy hydrocarbon feedstock is used for partial oxidation reactor 12, then gas cleaning plant 14 will produce only about half the amount of hydrogen which is required by methanol synthesizer 16. Accordingly, additional hydrogen from electrolysis unit 10 may be utilized in addition to the hydrogen from gas cleaning unit 14. Alternately, if the facility includes isobutylene synthesizer 20, then hydrogen which is produced by the isobutylene synthesizer 20 may be used as additional feed hydrogen for methanol synthesizer 16.

Methanol from methanol synthesizer 16 is fed via process stream 76 to ether synthesizer 18. As shown in FIG. 1, steam, water and isobutylene are fed via process streams 78, 80 and 82 respectively to synthesizer 18. Synthesizer 18 converts the isobutylene, methanol, steam and water to MTBE, heat and waste water designated by process streams 84, 86 and 88 respectively. In addition, as shown in FIG. 1 in dotted outline, ethanol may also be fed to ether synthesizer 18 to produce ETBE as well as MTBE. One particular advantage of this process is the production of ETBE. ETBE is more efficient as an oxygenate and an octane enhancer. However, these benefits are currently off set by the cost of producing ETBE. However, by feeding ethanol via process stream 122 into ether synthesizer 18, ETBE may be efficiently and cost effectively produced. In a further alternate embodiment, some or all of methanol 76 may be stored and sold as a commodity in the marketplace.

The MTBE may be transported via a pipe line to a storage vessel where it may be subsequently used in the facility or sold as a commodity in the marketplace.

Isobutylene for synthesizer 18 may be obtained as a commodity from the marketplace. Alternately, as shown in FIG. 1, isobutylene may be obtained from isomerization/isobutylene synthesizer 20. Process steam and butane are fed via process streams 90 and 92 respectively to isobutylene synthesizer 20 to produce isobutylene stream 82.

Overall, the process shown in FIG. 1 is a synergistic process for producing MTBE. The process is advantageous since it does not result in the release of green house gases to the environment. The process utilizes surplus energy and low value petro-chemical products to produce MTBE in a cost effective and non-polluting process.

Figure 2:
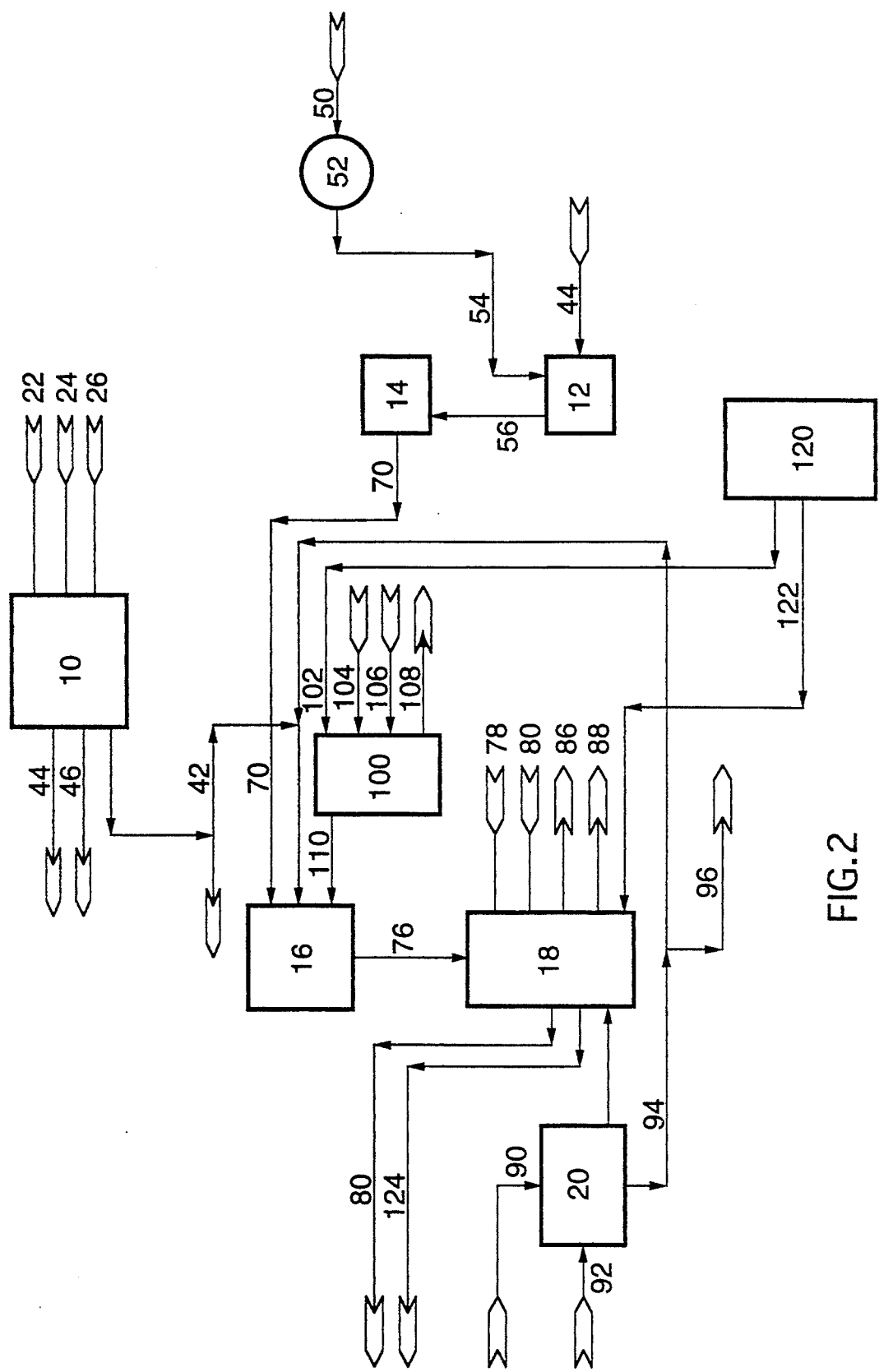
FIG. 2 is a schematic of a second embodiment of this process demonstrating the use of a producer gas plant to provide at least a part of the carbon monoxide constituent of the methanol synthesizer.

The potential sources for hydrogen for methanol synthesizer 16 are shown in more detail in FIG. 2. As shown in FIG. 2, hydrogen may be obtained from electrolysis unit 10 (process stream 42) and/or isobutylene synthesizer 20 (process stream 94). Hydrogen from electrolysis unit 10 (process stream 41) and excess hydrogen from isobutylene synthesizer 20 (process stream 76) may be fed to a central hydrogen storage (for example, storage tank 40 as shown in FIG. 6). The requisite amount of hydrogen may then be fed to methanol synthesizer 16. However, the hydrogen from each of these sources is of varying purity. Each of these may be stored individually for later use within the process or sold as a commodity in the marketplace. For example, as shown in FIG. 2, hydrogen from isobutylene synthesizer 20 and electrolysis unit 10 may each be separately stored and fed to methanol synthesizer 16 as required. Accordingly, hydrogen from electrolysis unit 10 is fed via process stream 41 to hydrogen storage tank 40. Hydrogen from isobutylene synthesizer 20 is fed via process stream 94 to methanol synthesizer 16. Excess hydrogen may be drawn from process stream 94 to storage facility via process stream 96 for later use or sale. Accordingly, methanol synthesizer may be fed with hydrogen from electrolysis unit 10 and/or isobutylene synthesizer 20.

In an alternate preferred embodiment, producer gas reactor 100 is also provided. Producer gas reactor 100 converts carbon dioxide to carbon monoxide by dissociation of the carbon dioxide to carbon monoxide and oxygen at elevated temperatures. Pursuant to this process, carbon dioxide is fed to producer gas reactor 100 via streams 102 and 104. Preferably, the carbon dioxide is at atmospheric pressure. Steam is supplied to producer gas reactor 100 via process stream 106. The steam is used to heat a bed in a reactor and the carbon dioxide is passed over or through the heated bed. The passage of the carbon dioxide over the bed heats the carbon dioxide to a temperature above the dissociation temperature of carbon dioxide (approximately 1100° C. at 1 atm). Waste steam is removed from the reactor by stream 108. The carbon monoxide from producer gas reactor 100 is used to supplement the carbon monoxide from partial oxidation reactor 12. This increase in the amount of feedstock of carbon monoxide to methanol synthesizer 16 may be used to increase the output of methanol from methanol synthesizer 16. The increase in the amount of carbon monoxide to methanol synthesizer 16 also requires the input of additional hydrogen. As discussed above, the hydrogen may be obtained by drawing down on the amount of hydrogen which may otherwise be sold as a by-product of the process. Preferably, the hydrogen which is utilized in methanol synthesizer 16 is derived from electrolysis plant 10 and/or isobutylene synthesizer 20.

Carbon dioxide for producer gas reactor 100 may be available from other processes within the facility. Exemplary of such a process is ethanol fermenter 120. Ethanol fermenter 120 produces ethanol, which is represented as process stream 122 in FIG. 2. A by-product of fermenter 120 is carbon dioxide which may be fed via process stream 102 to producer gas reactor 100. Alternately, an alternate source of carbon dioxide, such as that purchased in the marketplace, may be fed via process stream 104 to producer gas reactor 100.

One advantage of the addition of ethanol fermenter 120 is the expansion of ether synthesizer 18 to produce ETBE as well as MTBE. Accordingly, ether synthesizer 18 may include, in addition to a methanol reformer, an ethanol reformer to produce ETBE (process stream 124).

Figure 3:
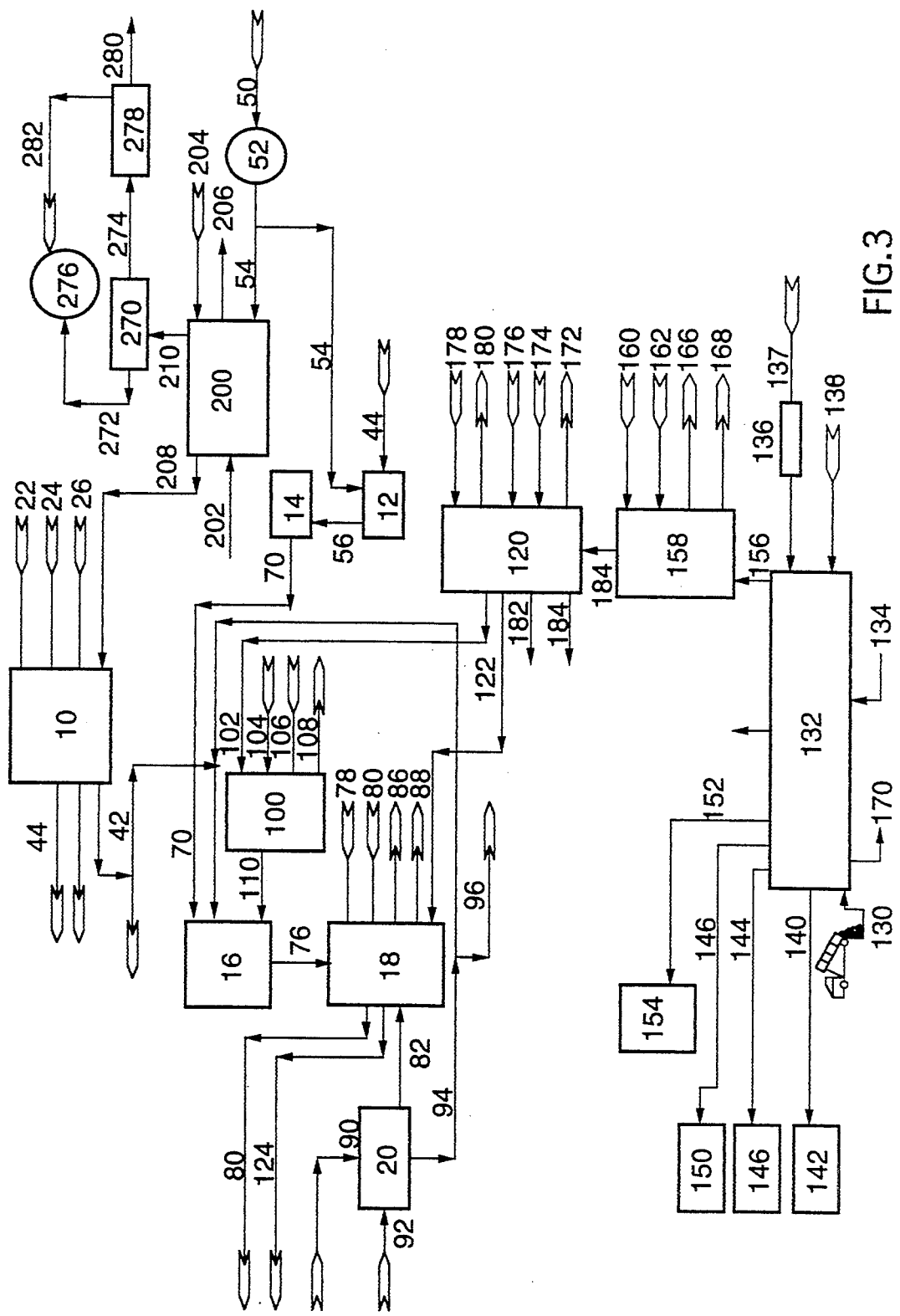
FIG. 3 is a schematic of a process flow sheet of a third embodiment of this process showing the production of ethanol.

A further alternate preferred embodiment is shown in FIG. 3. This embodiment shows modifications to the embodiment shown in FIG. 2. In one particular, the embodiment demonstrates a process for use of municipal solid waste to obtain a feedstock for ethanol fermenter 120.

As shown in FIG. 3, solid waste is provided via feed stream 130 to municipal solid waste separation unit 132. In addition, other natural source cellulose solid waste such as cob, news print, corn stover and wood waste may be fed via process stream 134 to municipal solid waste separation unit 132. Air and electricity are also fed to unit 132 via streams 136 and 138 respectively. The waste is segregated in unit 132 into various groups. These may include metals, organics, wood waste, plastics, cellulose and other less valuable products. Recovered metals may be sent via process stream 140 to compacting and salvaging unit 142. The product of unit 142 may be sold as scrap metal for use in recycling operations. Organic material such as kitchen and garden wastes may be fed via process stream 144 to fertilizer products forming unit 146. Recovered wood waste may be sent via process stream 148 to fibreboard forming unit 150. Recovered plastics may be fed via process stream 152 to plastics reforming unit 154. Cellulose may be fed via process stream 156 to cellulose preparation unit 158. Cellulose preparation unit 158 may use steam explosion processes such as those provided by Stake Technology Ltd. to produce cellulose for ethanol fermenter 120. Accordingly, electricity and high pressure steam are fed via process streams 160 and 162 to cellulose preparation unit 158. Unit 158 produces prepared cellulose (process stream 164), waste heat and waste water (process streams 166 and 168 respectively). Other low value materials may be fed via process stream 170 to a storage facility from which they may be shipped to a landfill site.

Prepared cellulose, cob, corn, or other feed material may be fed via process streams 164, 172 and 174 respectively to the ethanol fermenter. Steam and electricity are also fed via process streams 176 and 178 to ethanol fermenter 120. Ethanol fermenter 120 produces waste heat (process stream 180), waste water (process stream 182) and distillers dried grain (process stream 184).

As shown in FIG. 3, the process is also adaptable to including a cogeneration unit while still maintaining effectively negligible emissions of green house gases. In particular, the process may include a cogeneration unit 200. A hydrocarbon feedstock and air are combusted in the cogeneration unit to produce steam, electricity and flue gases. The hydrocarbon feedstock may be the same or different to that which is fed to the partial oxidation reactor. As shown in FIG. 3, the same source of hydrocarbon feedstock is utilized and accordingly a heavy oil is fed to cogeneration unit 200 via process stream 54. Air is fed to the cogeneration unit via process stream 202. Water is also supplied to the cogeneration unit via process stream 204. The cogeneration unit produces steam 206, electricity 208 and flue gases 210.

The cogeneration unit may utilize either a single cycle or combined cycle reactor. A typical combined cycle cogeneration process utilizing a combustion turbine is shown in FIG. 7 and a typical single cycle cogeneration process using a steam turbine is shown in FIG. 8.

Figure 7:
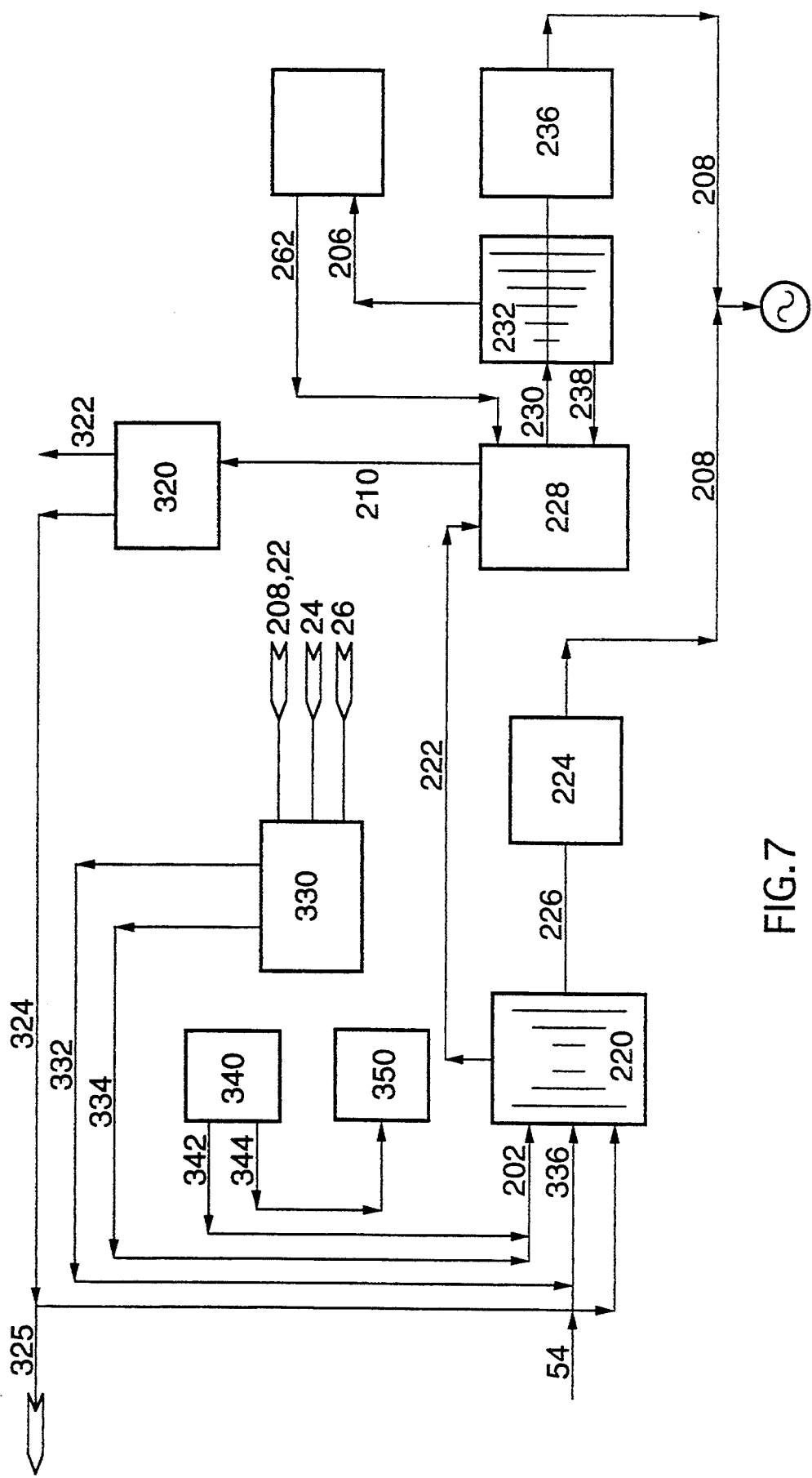
FIG. 7 is a schematic of a process flow sheet including a combined cycle cogeneration unit.
Figure 8:
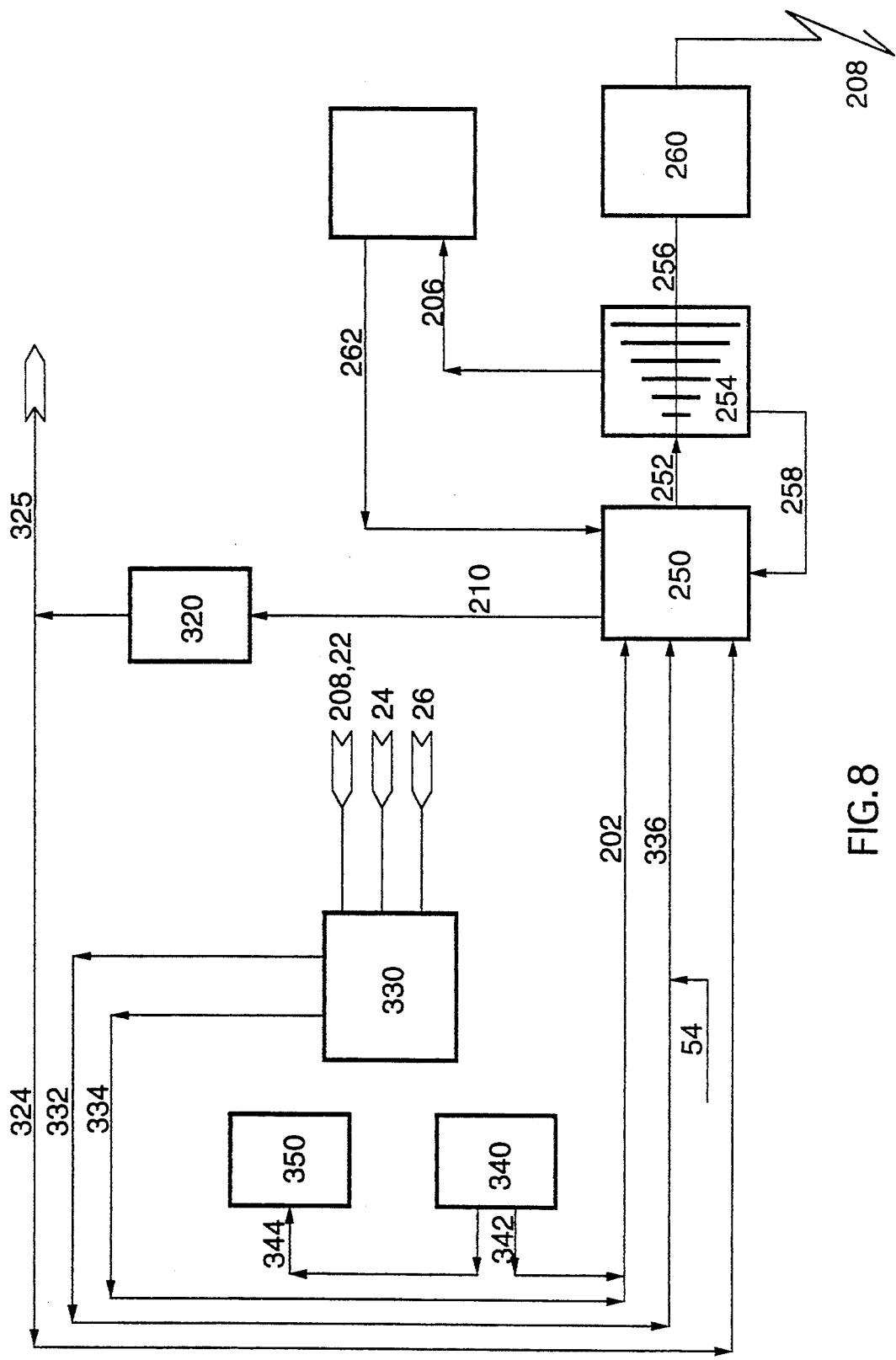
FIG. 8 is a schematic of a process flow sheet including a single cycle cogeneration unit.

Referring to FIG. 7, a combined cycle cogeneration process utilizes combustion turbine 220. Fuel 54 and air/oxygen 202 are fed into combustion turbine 220. The combustion of the fuel in combustion turbine 220 produces combustion gases 222 and power. The power is transmitted to generator 224 via power take-off 226. The rotation of the turbine is transmitted through power take-off 226 causing generator 224 to produce electricity 208. Combustion gas 222 from combustion turbine 220 is fed to heat recovery boiler 228. Heat recovery boiler 228 effectively acts as a heat exchanger transferring the heat from the combustion gas to water in the heat recovery boiler 228. The combustion gases, which have been cooled, are then vented from the boiler 228 as flue gases 210. The transfer of heat from combustion gases 222 to waste heat recovery boiler 228 produces steam 230. Steam 230 is fed to steam turbine 232. As steam 230 passes through steam turbine 232, the steam causes the turbine to rotate. This rotation is transmitted to generator 236 via power take-off 234 which causes generator 236 to produce electricity 208. As steam passes through steam turbine 232, part of the steam condenses and its condensate is returned to heat recovery boiler 228 via return stream 238. The remainder of the steam, which is at a lower temperature and pressure than steam 230, may be used as process steam in the industry or in alternate steps which are discussed above. The process steam is fed to the remainder of the industry via feed stream 206. The steam, which is used for heating purposes, is recycled to boiler 228 via return stream 240. Make up water is added to boiler 228 as required (not shown).

In conventional operation of a combustion turbine, nitrogen, an inert gas, is drawn into the turbine in conjunction with the oxygen component of the intake combustion air. This inert gas performs two functions. The heating of the inert gas by the combustion of the fuel causes it to expand and therefore raises its pressure. The inert gas exits the turbine causing the rotation of the blading and shaft assisting the combustion products to produce power. The inert gas also reduces the temperature of the combustion products to avoid injury to the metallurgy and materials of construction of the turbine 220 due to excessively elevated temperatures. Operation of these combustion turbines has evidenced that the use of nitrogen as the inert gas produces unacceptably high levels of the oxides of nitrogen, nitric oxide (NO) and nitrous oxide ($N_2O$), which combine with atmospheric moisture to produce acid rain components. Therefore, it is desirable to replace the nitrogen with an inert gas which does not contribute to acid rain.

In the instant process shown in FIG. 7, flue gas 210 principally comprises carbon dioxide cleaned in gas cleaning unit 320 and the cleaned flue gas is returned by flow stream 324 to the inlet of the combustion turbine. This procedure allows the exclusion of inlet nitrogen and air from the turbine inlet flow. The oxygen required for the combustion of the fuel can be provided, at least in part, from electrolysis 330, which may be a component of the electrolysis unit 10 shown in figures elsewhere herein or it may be an independent installation. Electrolysis unit 330 operates similarly to electrolysis 10 as shown above. Oxygen may be provided by flowstream 334 to the inlet of the combustion turbine to form, at least, a part of the combustion oxygen 202. Hydrogen produced by the electrolysis unit 330 may be fed by flowstream 332 to mix with the fuel 54 to form, at least, a part of hythane 336 to provide an enhanced fuel for the combustion turbine. Alternately, some or all of the oxygen required for the combustion of the fuel can be provided, at least in part, from air spearation plant 340. The oxygen derived from air separation plant 340 can be fed by flowstream 342 to the inlet of the combustion turbine. The nitrogen and other inert gases are conveyed by flowstream 334 to nitrogen storage 350 or to commercial sale.

Accordingly, the carbon dioxide circulating through the combustion turbine 220, flue gas stream 222, heat recovery boiler 228, flue gas stream 210, gas cleaning unit 320 and the carbon dioxide flowstream 324 becomes highly concentrated to essentially pure carbon dioxide. Accordingly, a portion of the carbon dioxide can be drawn off in flow stream 325 to be provided to the producer gas reactor to form, at least, a portion of feed stream 102 and/or to be provided to the partial oxidation reactor to form, at least, a portion of feed stream 300 and/or to be provided to storage and/or to commercial sale. Accordingly, concentrated carbon dioxide can be provided without the use of chemical or absorption separation facilities as required in conventional "single pass" combustion systems.

Referring to FIG. 8, single cycle cogeneration process utilizes steam boiler 250. Fuel 54 and air/oxygen stream 202 are fed into steam boiler 250. The combustion of the fuel in steam boiler 250 produces stack gases 210 and steam 252. Steam 252 is fed into steam turbine 254. As steam 252 passes through steam turbine 254, the steam causes the turbine to rotate. This rotation is transmitted to generator 260 via power take-off 256. The rotation of power take-off 256 causes generator 260 to produce electricity 208. As steam 252 passes through steam turbine 254, part of the steam condenses and this condensate is returned to boiler 250 via return stream 258. The remainder of the steam, which is at a lower temperature and pressure than steam 252, may be used as process steam in the industry or in alternate steps as discussed above. The process steam is fed to the remainder of the industry via stream 206. The steam which is used for heating purposes in the plant is recycled to steam boiler 250 via return stream 262. Make up water is added to steam boiler 250 as required (not shown).

The cogeneration reactor may be operated by an industry which requires process steam and electricity to run the industry. Accordingly, process steam 206 may be used in the industry for heating or other purposes as needed. Similarly, electricity 208 may be used in the industry or transmitted to a power grid (not shown) for sale to other consumers of electricity as needed. Alternately, part of the electricity may be used by electrolysis unit 10 to electrolyse water to produce hydrogen and oxygen as discussed above.

The flue gas of stream 210 is cleaned in gas cleaning unit 320 and returned in flowstream 324 to the inlet of the combustion turbine. In conventional operation of a steam boiler, nitrogen, an inert gas, is drawn into the boiler in conjunction with the oxygen component of the intake combustion air. The inert gas is used to reduce the temperature of the combustion products to avoid injury to the metallurgy and materials of construction of the boiler due to excessively elevated temperatures. Operation of these conventional steam boilers has evidenced that the use of nitrogen as the inert gas produces unacceptably high levels of the oxides of nitrogen, nitric oxide (NO) and nitrous oxide ($N_2O$), which combine with atmospheric moisture to produce acid rain components. Therefore, it is desirable to replace the nitrogen with an inert gas which does not contribute to acid rain.

In the embodiment shown in FIG. 8, the inert gas carbon dioxide, which is the principal component of flue gas stream 210, is cleaned in gas cleaning unit 320 and returned by flow stream 324 to the inlet of the boiler 250. This procedure allows the exclusion of inlet nitrogen and air from the boiler firing system. The oxygen required for the combustion of the fuel may be provided, at least in part, from water electrolysis unit 330, which may be a component of the electrolysis unit 10 shown in figures elsewhere herein or it may be an independent installation. Electrolysis unit 330 operates similarly to electrolysis unit 10 as shown above. The oxygen may be provided by flowstream 334 to the inlet of the boiler 250 to form, at least, a part of the combustion oxygen 202. The hydrogen produced by electrolysis unit 330 may be fed by flowstream 332 to mix with the fuel 54 to form, at least, a part of the fuel mixture 336 to provide an enhanced fuel for the steam boiler 250. Alternately, the oxygen required for the combustion of the fuel can be provided, at least in part, from air separation plant 340. The oxygen derived from the air separation plant 340 may be fed by flowstream 342 to the inlet of the boiler 250. The nitrogen and other inert gases are conveyed by flowstream 344 to nitrogen storage 350 or to commercial sale. Accordingly, the carbon dioxide circulating through the steam boiler 250, flue gas stream 210, gas cleaning unit 320 and carbon dioxide flowstream 324 becomes highly concentrated to essentially pure carbon dioxide. Accordingly, a portion of the carbon dioxide may be drawn off in flow stream 325 to be provided to the producer gas reactor to form, at least, a portion of feed stream 102 and/or to be provided to the partial oxidation reactor to form, at least, a portion of feed stream 300 and/or to be provided to storage and/or to commercial sale. Accordingly, concentrated carbon dioxide can be provided without the use of chemical or absorption separation facilities as required in conventional "single pass" combustion systems.

Figure 4:
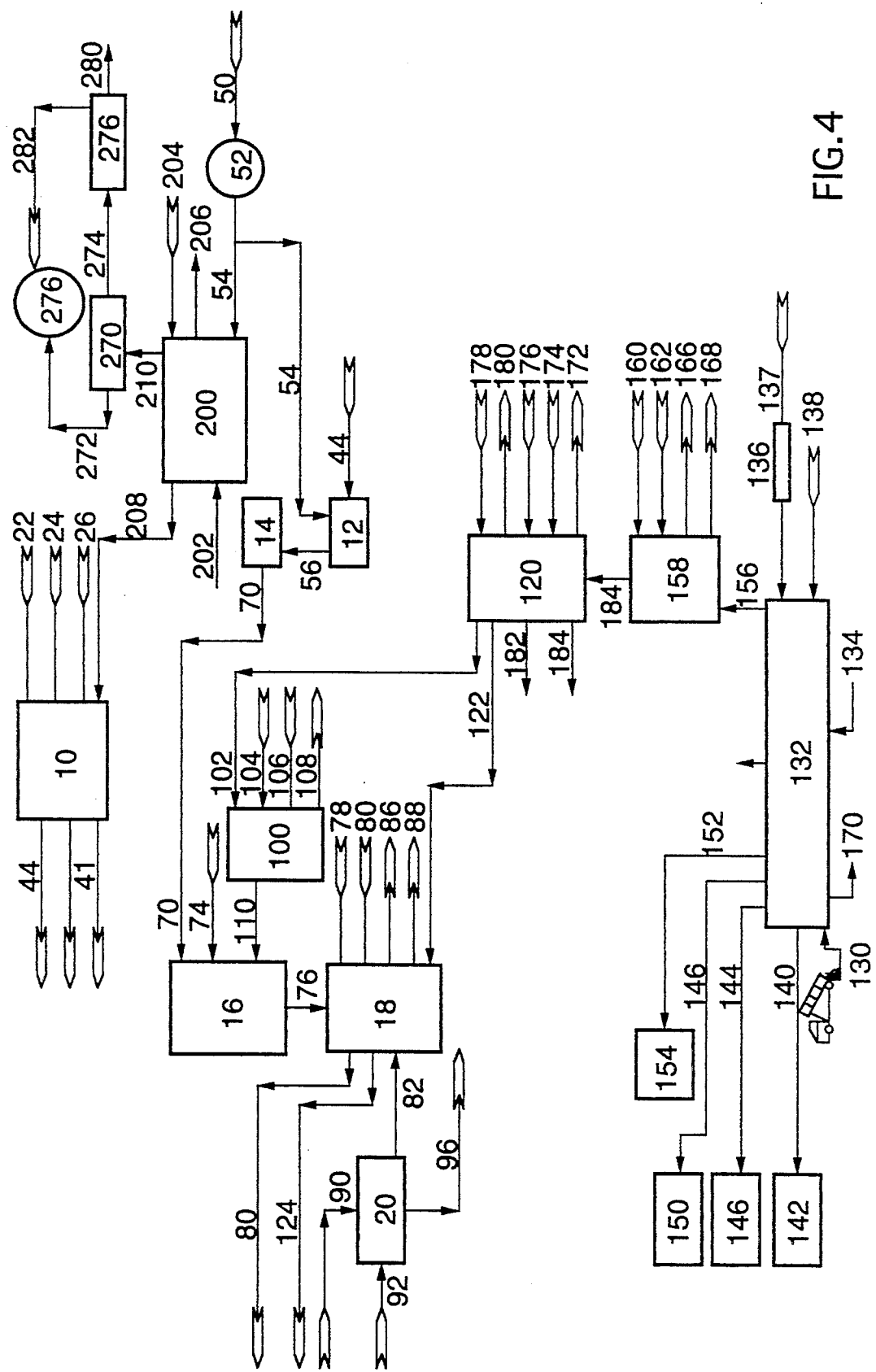
FIG. 4 is a variation of the schematic of FIG. 3.
Figure 10:
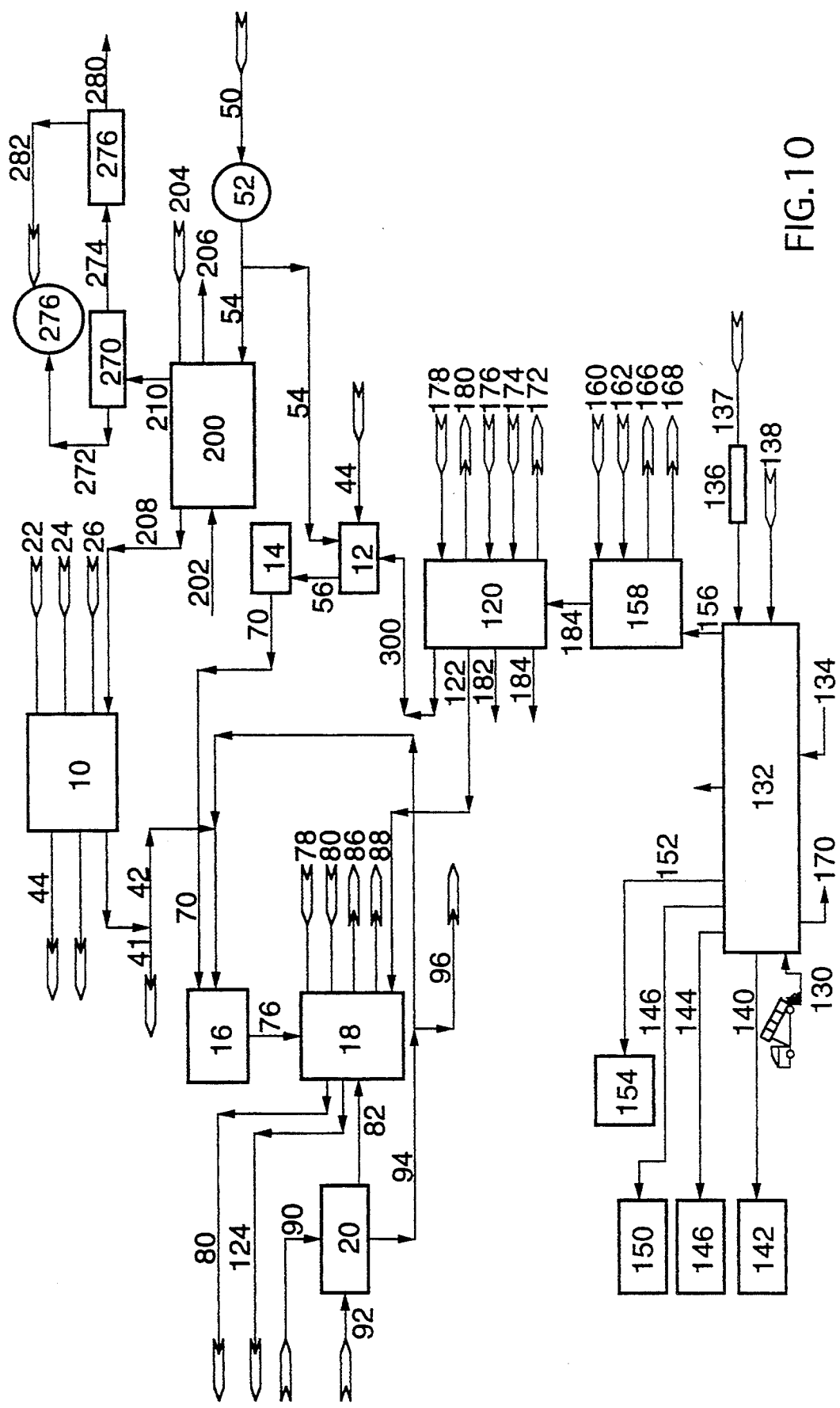
FIG. 10 is an alternate process schematic of the process of this invention; and, FIG. 11 is a further alternate process schematic of the process of the invention.

In alternate embodiments of FIGS. 3, 4 and 10, cogeneration unit 200 produces flue gases 210 principally comprised of carbon dioxide, water vapour, nitrogen and oxygen. In addition, lesser amounts of oxides of sulphur and nitrogen are also contained in flue gases 210. Flue gases 210 are cleaned in flue gas cleaning unit 270 by this process to produce a gaseous stream consisting substantially of oxygen and nitrogen (stream 272) and a gaseous stream of water vapour and $CO_2$, $H_2$, $SO_2$ and $SO_3$ (stream 274). Gaseous stream 272 may be safely vented to the atmosphere by stack 276. Gaseous stream 274 is fed to carbon dioxide stripping unit 278. In unit 278, stream 274 is treated to isolate the carbon dioxide. This results in the production of waste water stream 280 which may be disposed of or sent for further treatment and gaseous stream 282 which substantially comprises carbon dioxide. The carbon dioxide may be collected and sold as a commodity in the marketplace or used as feed material for producer gas plant 100 and/or partial oxidation reactor 12.

The use of producer gas reactor 100 provides an effective means to consume the carbon dioxide which is produced by the cogeneration unit. Accordingly, together with flue gas cleaning unit 270, the entire process remains a zero emission process for the production of methanol.

FIG. 4 shows a further alternate embodiment. In this alternate embodiment, the hydrogen from gas cleaning unit 14, the hydrogen from electrolysis unit 10, and the hydrogen from isobutylene synthesizer 20 (namely process streams 72, 42 and 94 respectively) are fed to a central reservoir where the hydrogen is pooled for use as may be required in methanol synthesizer or for sale in the marketplace. Also, as discussed above, due to the different qualities of process streams 72, 42 and 94, the hydrogen may be pooled collectively in one central storage tank or in a plurality of storage tanks to maintain, in isolation, each of the separate streams of hydrogen.

As will be appreciated from the foregoing, the rate of methanol production is dependent upon the rate of supply of carbon monoxide. Various sources are available for providing hydrogen to methanol synthesizer 16. The partial oxidation reactor may be the only source in the facility which generates carbon monoxide. As shown in the alternate embodiments of FIGS. 2, 3 and 4, ethanol fermenter 120, cogeneration unit 200 and producer gas reactor 100 may also be included in the facility. The cogeneration unit and the ethanol fermenter both provide sources of carbon dioxide. Producer gas reactor 100 converts the carbon dioxide from either of these sources, or alternately, carbon dioxide which is bought in the marketplace, to carbon monoxide. Accordingly, producer gas reactor 100 may become a bottleneck in the rate of production of methanol and, accordingly, MTBE and/or ETBE.

According to the instant invention, an improvement is also disclosed for partial oxidation reactor 12. Pursuant to this improvement, the reliance upon additional carbon monoxide produced by producer gas reactor 100 is reduced and, in some cases, producer gas reactor 100 may not be required.

Figure 5:
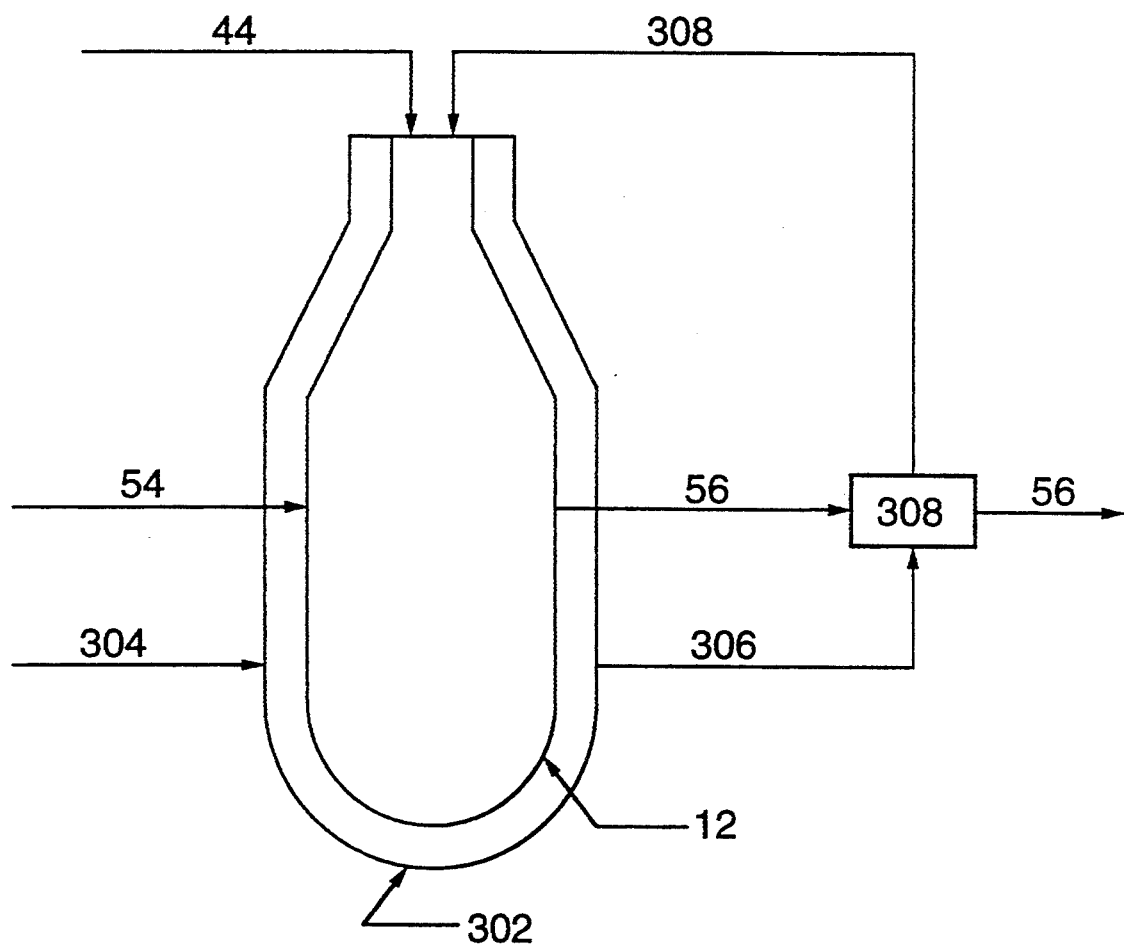
FIG. 5 is an alternate process schematic for the partial oxidation reactor.

Referring to FIG. 5, oxygen is fed to partial oxidation reactor 12 via process stream 44. The hydrocarbon feedstock is fed to partial oxidation reactor 12 via process stream 54. Partial oxidation reactor 12 produces gas stream 56. Pursuant to the improvement, partial oxidation reactor 12 is provided with cooling jacket 302. Carbon dioxide is fed to cooling jacket 302 via stream 304. The carbon dioxide may be obtained from ethanol fermenter 120, cogeneration unit 200 or may be obtained from the marketplace. The carbon dioxide in cooling jacket 302 is heated to an elevated temperature. The heated carbon dioxide is then fed via stream 306 to indirect heat exchanger 308. Gaseous stream 56 is also fed to heat exchanger 308. During its passage through heat exchanger 308, the carbon dioxide stream is further heated and gaseous stream 56 is cooled. By this process, the carbon dioxide is heated to or above the dissociation temperature of carbon dioxide (above about 1100° C., more preferably, above about 1250° C.). At this temperature, carbon dioxide dissociates to produce carbon monoxide and oxygen. Stream 308 is then fed into partial oxidation reactor 12. By this process, carbon dioxide from a source internal or external to the facility is converted to carbon monoxide and oxygen using available waste heat in the partial oxidation reactor. Accordingly, additional hydrocarbon feedstock is not required to produce an increased amount of carbon monoxide.

Figure 9:
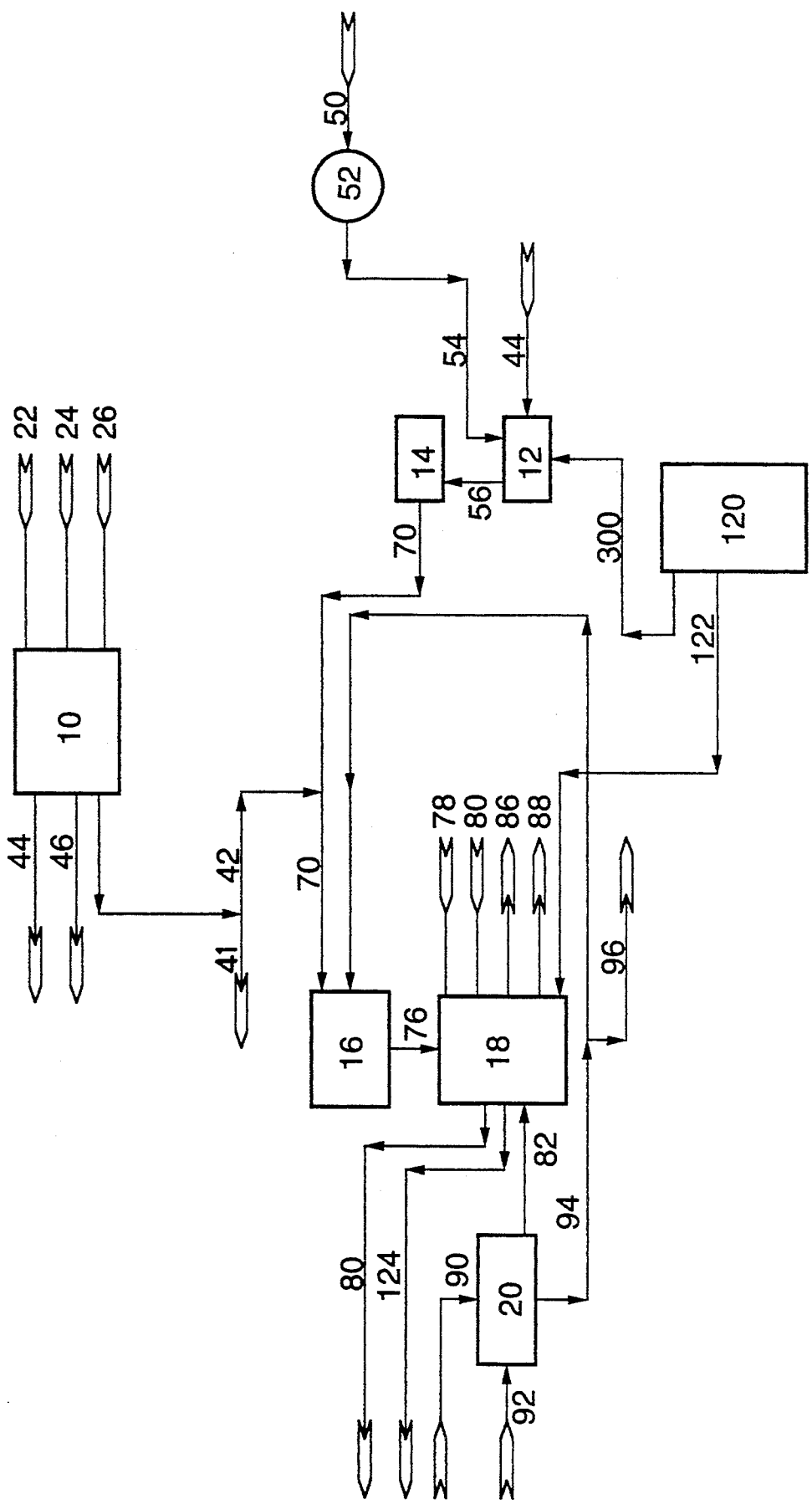
FIG. 9 is a variation of the schematic of FIG. 2.

FIG. 9 shows an example of this latter embodiment and demonstrates a variation of the schematic of FIG. 2 demonstrating the use of the partial oxidation reactor of FIG. 5 to convert the carbon dioxide into carbon monoxide absent the use of the producer gas reactor. However, in this embodiment, the carbon dioxide produced in ethanol reactor 120 is fed via process stream 300 to cooling jacket 302 and enters cooling jacket 302 via process stream 304. As will be appreciated, ethanol reactor 120 may be only one of a number of potential sources of carbon dioxide for cooling jacket 302.

FIG. 10 is a further example of this latter embodiment. This figure embodiment differs to the embodiment of FIG. 3 by using the partial oxidation reactor of FIGS. 5 and 9 to convert the carbon dioxide into carbon monoxide in addition to or alternatively absent the use of the producer gas reactor.

Figure 11:
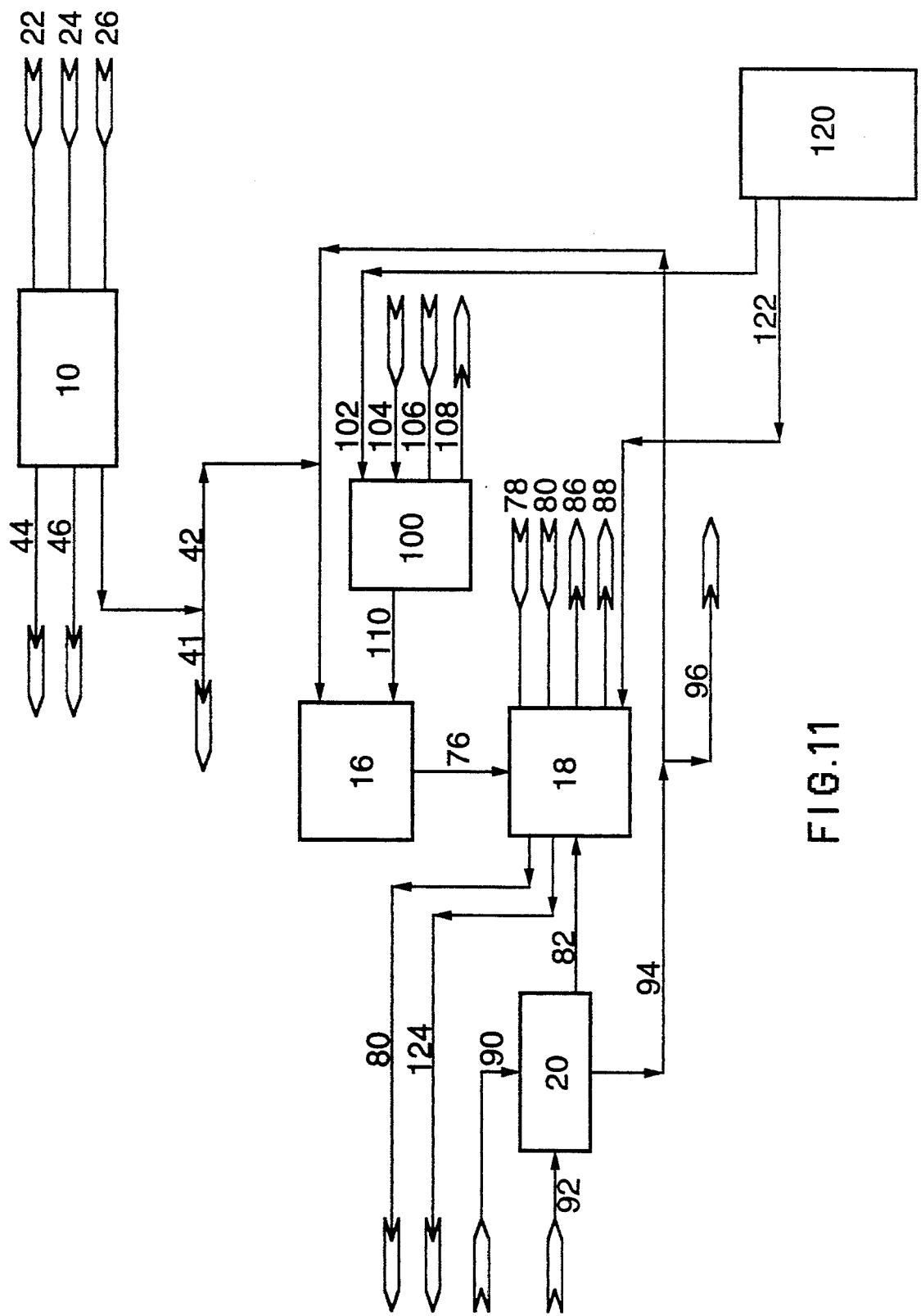

FIG. 11 shows a further alternate preferred embodiment which is similar to that shown in FIG. 2. In this embodiment, all of the carbon monoxide for methanol synthesizer 16 is obtained from producer gas reactor 100. Accordingly, partial oxidation reactor 12 and gas cleaning unit 14 are not required.

Accordingly, an advantage of the instant invention is that the process may become effectively a sponge for carbon dioxide, one of the key green house gases. By the modification of the partial oxidation reactor, as shown in FIG. 5, or the inclusion of producer gas reactor 100, carbon dioxide is converted to carbon monoxide and subsequently converted in methanol synthesizer 16 to produce methanol. The methanol is subsequently converted to produce MTBE. Thus, a green house gas is efficiently and effectively converted into MTBE which may be used as an oxygenate in gasoline to improve combustion.

EXAMPLE 1

100 megawatts of electricity is supplied to electrolysis unit 10. Electrolysis unit 10 utilizes this electricity to produce 3,800 lbs/hr of hydrogen, 85 lbs/hr of heavy water and 29,860 lbs/hr of oxygen. The oxygen together with 26,330 lbs/hr of gas oil or #6 oil is fed to the partial oxidation reactor 12. Partial oxidation reactor 12 produces 56,160 lbs/hr of off gases which are fed to gas cleaning unit 14. Gas cleaning unit 14 produces 3,513 lbs/hr of hydrogen and 52,253 lbs/hr of carbon monoxide. The carbon monoxide, together with 7,465 lbs/hr of hydrogen is fed to the methanol synthesizer 16. Methanol synthesizer 16 produces 59,717 lbs/hr of methanol. The methanol is fed to a ether synthesizer 18. 108,237 lbs/hr of butane are fed to the isobutylene synthesizer. The isobutylene synthesizer produces 3,732 lbs/hr of hydrogen and 104,505 lbs/hr of isobutylene. The isobutylene is fed to the ether synthesizer 18 together with the methanol. The ethers synthesizer produces 164,222 lbs/hr of MTBE.

EXAMPLE 2

Example 2 demonstrates the facility shown in FIG. 4 which is designed to produce 380 million liters per year of methanol. 100 megawatts of electricity is applied to electrolysis unit 10 to produce 3,800 lbs/hr of hydrogen, 85 lbs/hr of heavy water and 30,400 lbs/hr of oxygen. 26,330 lbs/hr of gas oil or #6 oil and 29,860 lbs/hr of oxygen are supplied to the partial oxidation reactor 12. The resulting gases are fed to gas cleaning unit 14 which produces 52,253 lbs/hr of carbon monoxide and 3,513 lbs/hr of hydrogen. These gases, together with the hydrogen produced in electrolysis unit 10 and 4,527 lbs/hr of hydrogen produced in the isobutylene synthesizer are fed to the methanol synthesizer. Producer gas reactor 100 is fed 24,066 lbs/hr of carbon dioxide from a 100 million liter per year ethanol fermenter. In addition, 6,566 lbs/hr of carbon dioxide is fed to the producer gas reactor 100 to produce 30,630 lbs/hr of carbon monoxide. This carbon monoxide is also supplied to methanol synthesizer 16. Methanol synthesizer 16 produces 94,723 lbs/hr of methanol which is supplied to the ether synthesizer.

171,686 lbs/hr of butane are fed to the isobutylene synthesizer to produce 5,920 lbs/hr of hydrogen and 165,766 lbs/hr of isobutylene. As discussed above, 4,527 lbs/hr of the hydrogen are fed to the methanol synthesizer and 1,393 lbs/hr of hydrogen is sent to storage. The isobutylene and methanol is combined in the ether synthesizer to produce 260,500 lbs/hr of MTBE.

EXAMPLE 3

This example demonstrates the embodiment shown in FIG. 3 which is a facility to produce 240 million liters per year of methanol.

84,000 lbs/hr of gas oil or #6 oil, 297,577 lbs/hr of oxygen and 984,980 lbs/hr of nitrogen are supplied to an 80 megawatts cogeneration unit 200. Atmospheric air is utilized as the source of oxygen and nitrogen. 120% oxygen is supplied to cogeneration unit 200. The plant produces 1.2 million lbs/hr of 180 psi steam and flue gases. The electricity from cogeneration unit 200 and 100 megawatts of electricity obtained from a power utility are provided to electrolysis unit 10 to produce 3,800 lbs/hr of hydrogen, 85 lbs/hr of heavy water and 30,400 lbs/hr of oxygen. The remainder of the flow rates for the methanol synthesizer 16, the producer gas reactor 100, the ether synthesizer 18 and the isobutylene synthesizer are the same as in Example 2.

The flue gases from cogeneration unit 200 comprise mixed streams of oxygen, nitrogen, carbon dioxide, water vapour and sulphur species which are separated in flue gas cleaning unit 278 as follows. Flue gas cleaning 278 produces 984,980 lbs/hr of nitrogen and 49,596 lbs/hr of oxygen which is vented to the atmosphere. 75,600 lbs/hr of water and 2,500 lbs/hr of sulphur species are also produced and treated in the water treatment plant. The water treatment plant produces 252,787 lbs/hr of carbon dioxide.

We claim:

1. A synergistic process for the production of methanol comprising the steps of:
   (a) electrolysing water to produce hydrogen and oxygen;
   (b) providing a feed stream of an organic combustible fuel;
   (c) feeding at least a portion of the oxygen produced in step (a) together with a stoichiometric amount of said organic combustible fuel to a partial oxidation reactor to produce off gases including carbon monoxide and hydrogen;
   (d) feeding at least a portion of said carbon monoxide and hydrogen to a methanol synthesizer to produce methanol; and,
   (e) adding additional hydrogen to said methanol synthesizer to provide a stoichiometric feed of hydrogen and carbon monoxide to said methanol synthesizer.

2. The process as claimed in claim 1 wherein said fuel is a heavy oil having a boiling point above 650° F.

3. The process as claimed in claim 2 wherein said heavy oil has a boiling point above 1000° F.

4. The process as claimed in claim 2 further comprising the step of reacting at least a portion of said methanol in an ether synthesizer to produce methyl tertiary butyl ether.

5. The process as claimed in claim 4 further comprising the steps of:
   (a) combining steam and butane in an isobutylene synthesizer to produce hydrogen and isobutylene; and,
   (b) feeding at least a portion of said isobutylene to said ether synthesizer to produce said methyl tertiary butyl ether.

6. The process as claimed in claim 1 wherein said additional hydrogen which is fed to said methanol synthesizer is produced in step (a) of claim 1.

7. The process as claimed in claim 6 wherein said additional hydrogen which is fed to said methanol synthesizer is selected from the hydrogen produced by said electrolysis in step (a) of claim 1, the hydrogen produced by said isobutylene synthesizer or a mixture thereof.

8. The process as claimed in claim 1 further comprising the steps of:
   (a) providing a feed stream of carbon dioxide;
   (b) heating said carbon dioxide to a temperature above the dissociation temperature of said carbon dioxide to produce carbon monoxide; and,
   (c) providing at least a portion of said carbon monoxide produced in step (a) to said methanol synthesizer.

9. The process as claimed in claim 8 wherein said process also includes the steps of:
   (a) adding steam and an ethanol fermenter feedstock to an ethanol fermenter to produce ethanol;
   (b) reacting at least a portion of said ethanol to produce ethyl tertiary butyl ether; and,
   (d) providing at least a portion of said carbon dioxide from said fermenter to said reactor of step (a) of claim 8.

10. The process as claimed in claim 1 further comprising the steps of:
    (a) adding steam and an ethanol fermenter feedstock to an ethanol fermenter to produce ethanol; and,
    (b) reacting at least a portion of said ethanol to produce ethyl tertiary butyl ether.

11. The process as claimed in claim 1 further comprising the steps of:
    (a) providing a first feed stream comprising an organic combustible fuel;
    (b) providing a second feed stream comprising oxygen;
    (c) introducing said first and second feed streams into a cogeneration reactor for combusting said first feed stream and producing steam, electricity and stack gases containing carbon dioxide; and,
    (d) using at least a portion of said electricity to electrolyse water in step (a) of claim 1.

12. The process as claimed in claim 11 further comprising the steps of:
    (a) treating said stack gases to obtain a first stream comprising sulphur containing compounds and water vapour and a second stream comprising carbon dioxide; and,
    (b) feeding at least a portion of said second stream into said cogeneration reactor.

13. The process as claimed in claim 12 wherein said cogeneration reactor is a single cycle reactor having a steam boiler and said second stream is fed to said steam boiler.

14. The process as claimed in claim 12 wherein said cogeneration reactor is a combined cycle reactor having a combustion turbine and said second stream is fed to said combustion turbine.

15. The process as claimed in claim 12 further comprising an air separation plant to produce a first stream comprising oxygen and a second stream comprising nitrogen and at least a portion of said first stream is fed to said cogeneration reactor.

16. The process as claimed in claim 12 wherein said second stream consists essentially of carbon dioxide.

17. The process as claimed in claim 11 further comprising the steps of:
    (a) providing a feed stream of carbon dioxide;
    (b) heating said carbon dioxide to a temperature above the dissociation temperature of said carbon dioxide to produce carbon monoxide; and,
    (c) providing at least a portion of said carbon monoxide produced in step (a) to said methanol synthesizer.

18. The process as claimed in claim 17 wherein carbon dioxide from said stack gases is isolated and supplied to said reactor of step (a) of claim 17.

19. The process as claimed in claim 5 wherein said off gases comprising hydrogen, and said hydrogen is separated from said off gases.

20. The process as claimed in claim 5 further comprising the steps of:
    (a) providing a feed stream of carbon dioxide;

(b) heating said carbon dioxide to a temperature above the dissociation temperature of said carbon dioxide to produce carbon monoxide; and, (c) providing at least a portion of said carbon monoxide produced in step (a) to said methanol synthesizer.

21. The process as claimed in claim 20 wherein the hydrogen which is fed to said methanol synthesizer is selected from the hydrogen produced by said electrolysis of step (a) of claim 1, the hydrogen produced in said isobutylene synthesizer or a combination thereof.

22. The process as claimed in claim 21 further comprising the steps of:

(a) adding steam and an ethanol fermenter feedstock to an ethanol fermenter to produce ethanol and carbon dioxide;

(b) isolating said carbon dioxide; and, (c) supplying said carbon dioxide to said reactor of step (a) of claim 17.

23. The process as claimed in claim 21 further comprising the steps of:

(a) adding steam and an ethanol fermenter feedstock to an ethanol fermenter to produce ethanol and carbon dioxide; and, (b) reacting at least a portion of said ethanol to produce ethyl tertiary butyl ether.

24. The process as claimed in claim 23 further comprising the steps of:

(a) isolating said carbon dioxide produced in said fermenter; and, (c) providing carbon dioxide selected from the group consisting of carbon dioxide from said fermenter, and carbon dioxide from said stack gases or a mixture thereof to said reactor of step (a) of claim 20.

25. A synergistic process for the production of methanol comprising the steps of:

(a) electrolysing water to produce hydrogen and oxygen;

(b) providing a feed stream of an organic combustible fuel;

(c) feeding at least a portion of the oxygen produced in step (a) together with a stoichiometric amount of said organic combustible fuel to a partial oxidation reactor to produce off gases including carbon monoxide and hydrogen;

(d) providing a feed stream of carbon dioxide to said partial oxidation reactor so as to elevate the temperature of said carbon dioxide to a temperature above the dissociation temperature of said carbon dioxide to produce carbon monoxide and oxygen;

(e) feeding said carbon monoxide and oxygen produced in step (d) to said partial oxidation reactor to produce additional amounts of carbon monoxide, hydrogen and heat;

(f) feeding at least a portion of said carbon monoxide and hydrogen to a methanol synthesizer to produce methanol; and, (g) adding additional hydrogen to said methanol synthesizer to provide a stoichiometric feed of hydrogen and carbon monoxide to said methanol synthesizer.

26. The process as claimed in claim 25 wherein said carbon dioxide is also used to cool the off gases from said partial oxidation reactor.

27. A synergistic process for the production of methanol comprising the steps of:

(a) electrolysing water to produce hydrogen and oxygen;

(b) providing a feed stream of carbon dioxide;

(c) heating said carbon dioxide to a temperature above the dissociation temperature of said carbon dioxide to produce carbon monoxide; and, (d) providing a stoichiometric amount of carbon monoxide and hydrogen to a methanol synthesizer to produce methanol, said stoichiometric amount being obtained by utilizing at least a portion of the carbon monoxide prepared by step (c) above and at least a portion of the hydrogen prepared in step (a) above.

28. The process as claimed in claim 27 further comprising the step of reacting at least a portion of said methanol in an ether synthesizer to produce methyl tertiary butyl ether.

29. The process as claimed in claim 28 further comprising the steps of:

(a) combining steam and butane in an isobutylene synthesizer to produce hydrogen and isobutylene; and, (b) feeding at least a portion of said isobutylene to said ether synthesizer to produce said methyl tertiary butyl ether.

30. The process as claimed in claim 29 wherein said hydrogen which is fed to said methanol synthesizer is selected from the hydrogen produced by said electrolysis in step (a) of claim 22, and the hydrogen produced by said isobutylene synthesizer or a mixture thereof.

31. The process as claimed in claim 30 further comprising the steps of:

(a) adding steam and an ethanol fermenter feedstock to an ethanol fermenter to produce ethanol and carbon dioxide; and, (b) reacting at least a portion of said ethanol to produce ethyl tertiary butyl ether.

32. The process as claimed in claim 31 wherein at least a portion of the carbon dioxide produced in said fermenter is used to prepare feed stream (b) of claim 27.

33. The process as claimed in claim 27 further comprising the steps of:

(a) adding steam and an ethanol fermenter feedstock to an ethanol fermenter to produce ethanol and carbon dioxide; and, (b) reacting at least a portion of said ethanol to produce ethyl tertiary butyl ether.

34. The process as claimed in claim 33 wherein at least a portion of the carbon dioxide produced in said fermenter is used to prepare feed stream (b) of claim 27.

* * * * *